United States Patent [19]
Mansat et al.

[11] Patent Number: 5,944,758
[45] Date of Patent: Aug. 31, 1999

[54] SHOULDER PROSTHESIS

[75] Inventors: Michel Mansat, Toulouse Cedex, France; Otto Sneppen, Aarhus, Denmark; Ian G. Kelly, Glasgow, United Kingdom; Pierre Hoffmeyer, Geneve, Switzerland

[73] Assignee: Minnesota Mining and Manufacturing Company, St. Paul, Minn.

[21] Appl. No.: 08/946,758

[22] Filed: Oct. 8, 1997

[51] Int. Cl.$^6$ .................................................. A61F 2/40
[52] U.S. Cl. ................... 623/19; 623/18; 623/22
[58] Field of Search ................... 623/18, 19, 22, 623/23

[56] References Cited

U.S. PATENT DOCUMENTS

| | | | |
|---|---|---|---|
| 3,916,451 | 11/1975 | Buechel et al. | 3/1.91 |
| 3,978,528 | 9/1976 | Crep | 3/1.91 |
| 4,003,095 | 1/1977 | Gristina | 3/1.91 |
| 4,040,131 | 8/1977 | Gristina | 3/1.91 |
| 4,179,758 | 12/1979 | Gristina | 3/1.91 |
| 4,206,517 | 6/1980 | Pappas et al. | 3/1.91 |
| 4,219,893 | 9/1980 | Noiles | 3/1.911 |
| 4,279,041 | 7/1981 | Buchholz | 3/1.912 |
| 4,301,553 | 11/1981 | Noiles | 3/1.911 |
| 4,352,212 | 10/1982 | Greene et al. | 3/1.91 |
| 4,538,305 | 9/1985 | Engelbrecht et al. | 623/20 |
| 4,549,319 | 10/1985 | Meyer | 623/18 |
| 4,608,053 | 8/1986 | Keller | 623/23 |
| 4,634,444 | 1/1987 | Noiles | 623/20 |
| 4,650,489 | 3/1987 | Thompson | 623/16 |
| 4,693,723 | 9/1987 | Gebard | 623/19 |
| 4,822,370 | 4/1989 | Schelhas | 623/23 |
| 4,865,605 | 9/1989 | Dines et al. | 623/19 |
| 4,892,546 | 1/1990 | Kotz et al. | 623/18 |
| 4,908,032 | 3/1990 | Keller | 623/18 |
| 4,911,719 | 3/1990 | Merle | 623/18 |
| 4,919,669 | 4/1990 | Lannelongue | 623/19 |
| 4,919,670 | 4/1990 | Dale et al. | 623/19 |
| 4,938,773 | 7/1990 | Strand | 623/23 |
| 4,957,510 | 9/1990 | Cremascoli | 623/23 |
| 4,963,155 | 10/1990 | Lazzeri et al. | 623/23 |

(List continued on next page.)

FOREIGN PATENT DOCUMENTS

| | | |
|---|---|---|
| 0 041 591 A1 | 12/1981 | European Pat. Off. . |
| 0 127 503 | 12/1984 | European Pat. Off. . |
| 0 201 407 A1 | 11/1986 | European Pat. Off. . |
| 0 216 489 | 4/1987 | European Pat. Off. . |
| 0 278 807 | 8/1988 | European Pat. Off. . |
| 0 299 889 A3 | 1/1989 | European Pat. Off. . |

(List continued on next page.)

OTHER PUBLICATIONS

"Surgical Protocol Modular Shoulder" brochure, 3M Health Care Limited 1994.
"Product Specification" brochure, 3M Health Care Limited 1994.
"3M Modular Shoulder Ideas in Motion" brochure, 3M Health Care Limited 1994.
"Neer II Total Shoulder System" brochure, 3M Health Care Limited 1989.
Glenohumeral Arthroplasty, pp. 148–150.

(List continued on next page.)

*Primary Examiner*—Michael J. Milano
*Attorney, Agent, or Firm*—Robert W. Sprague; Eloise J. Maki; Stephen W. Bauer

[57] ABSTRACT

A proximal humeral prosthesis that is particularly designed for treating a fractured humerus. The prosthesis comprises a head corresponding to the humeral head of a patient, and a stem having a proximal end to which the head is mounted. The prosthesis has a central plane coincident with the longitudinal axis of the stem about which it has a mirror axis of symmetry. One, or preferably pair of, projecting ribs are positioned at or near the proximal end of the stem adjacent the head. The projecting ribs are offset in opposite directions relative to the center plane at substantially identical offset angles (e.g., about 20° to about 40°) approximating the greater or lesser tuberosity of the humerus. Also disclosed is a method of treating a fractured humerus with this prosthesis.

26 Claims, 2 Drawing Sheets

U.S. PATENT DOCUMENTS

| | | | |
|---|---|---|---|
| 4,986,833 | 1/1991 | Worland | 623/19 |
| 5,002,578 | 3/1991 | Luman | 623/23 |
| 5,201,882 | 4/1993 | Paxson | 623/23 |
| 5,282,865 | 2/1994 | Dong | 623/19 |
| 5,358,526 | 10/1994 | Tornier | 623/19 |
| 5,462,563 | 10/1995 | Shearer et al. | 623/18 |
| 5,489,309 | 2/1996 | Lackey et al. | 623/19 |
| 5,507,817 | 4/1996 | Craig et al. | 623/18 |
| 5,507,818 | 4/1996 | McLaughlin | 623/18 |
| 5,549,682 | 8/1996 | Roy | 623/19 |
| 5,658,340 | 8/1997 | Muller et al. | 623/19 |
| 5,702,486 | 12/1997 | Craig et al. | 623/23 |
| 5,728,161 | 3/1998 | Camino et al. | 623/19 |

FOREIGN PATENT DOCUMENTS

| | | |
|---|---|---|
| 0 299 889 B1 | 1/1989 | European Pat. Off. . |
| 0 485 311 A1 | 5/1992 | European Pat. Off. . |
| 0 599 429 A2 | 6/1994 | European Pat. Off. . |
| 0 639 359 A1 | 2/1995 | European Pat. Off. . |
| 0 664 108 | 7/1995 | European Pat. Off. . |
| 0 679 375 A1 | 11/1995 | European Pat. Off. . |
| 0 712 617 A1 | 5/1996 | European Pat. Off. . |
| 2 617 706 | 1/1989 | France . |
| 2 647 670 | 12/1990 | France . |
| 2 652 498 | 4/1991 | France . |
| 2 664 809 A1 | 1/1992 | France . |
| 2 721 200 | 12/1995 | France . |
| 29 32 744 | 2/1980 | Germany . |
| 44 01 952 | 5/1995 | Germany . |
| 195 09 037 C1 | 9/1996 | Germany . |
| 1 292 561 | 1/1971 | United Kingdom . |
| 1 438 950 | 6/1976 | United Kingdom . |
| 1 548 750 | 7/1979 | United Kingdom . |
| 2 223 172 | 4/1990 | United Kingdom . |
| WO 94/15551 | 7/1994 | WIPO . |
| WO 95/22302 | 8/1995 | WIPO . |
| WO 96/17553 | 6/1996 | WIPO . |
| WO 96/38104 | 12/1996 | WIPO . |
| WO 96/41597 | 12/1996 | WIPO . |

OTHER PUBLICATIONS

Biomet, Inc.—Shoulder Systems, http://www.biomet/com/product/shoulder,html ((c) 1997), plus pages on Bio–Modular™, Bi–Angular™, Bi–Angular/Bi–Polar™, Integrated Shoulder System™, and Proximal Humeral Replacement™.

DePuy, Product Information: Global™ Total Shoulder System, http://www.depuy.com/products/global.htm (last updated Mar. 13, 1998).

Homedica: MRS, http://www.howmedica.com/mrs/shoulder.htm, http://www.howmedica.com/mrs/shoulder1.htm, http://www.howmedica.com/mrs/shoulder2.htm, http://www.howmedica.com/mrs/shoulder3.htm (printed May 29, 1998).

Daniel E. Williamson, M.S., Design Considerations in Total Shoulder Arthroplasty Relating to Long–Term Glenohumeral Stability ((c) 1994 Biomet, Inc.).

"Anatomic Determination of Humeral Head Retroversion: The Relationship of the Central Axis of the Humeral Head to the Bicipital Groove", pp. 255–256, Tillet et al., J. Shoulder Elbow Surg., Sep/Oct. 1993.

"The Biomechanical Effects of Malposition of Tuberosity Fragments on the Humeral Prosthetic Reconstruction for Four Part Proximal Humerus Fractures", p. 1148, 44th Annual Meeting, Orthopaedic Research Society, Mar. 16–19, New Orleans, Louisiana.

"Comparison of Humeral Head Retroversion with the Humeral Axis/Biceps Groove Relationship: A Study in Live Subjects and Cadavers", pp. 453–457, Doyle and Burks, J. Shoulder Elbow Surg, vol. 7, No. 5.

SHOULDER PROSTHESIS

This invention relates to a shoulder prosthesis, and in particular to that part of the prosthesis which will replace the humeral head at the proximal end of the arm.

BACKGROUND OF THE INVENTION

Shoulder replacement is a well-known and widely used technique which has been very successful. This is particularly important where the patient has disabling pain which is unresponsive to normal treatments and where the humeral head has suffered from osteoarthritis, rheumatoid arthritis and so on. In addition, a shoulder replacement may also be required following acute trauma situations where the humeral head has been fractured. In such circumstances frequently the bone in that area has been fractured into several pieces including separation of the humeral head or separation of the head and the greater and lesser tuberosities from the main part of the humerus.

The proximal humerus in many prior systems comprises a head and a stem and a number of radially directed ribs are provided at the proximal end. These have a strengthening function, and once the stem has been implanted into the proximal end of the humerus, they help to ensure that the stem cannot rotate relative the humerus. Such ribs include a lateral rib, a strengthening and supporting rib for the humeral head which is diametrically opposite this lateral rib, and, at right angles to these two ribs, a further pair of ribs that have a strengthening effect. The lateral rib is usually provided with a number of small holes, which can be used to suture a separated greater and/or lesser tuberosity into place to allow union with the main part of the bone if they have been fractured or osteotomised.

We have found in practice, however, that there are occasions when it is quite difficult to suture the greater and lesser tuberosities in place. This is particularly true when trying to tie a lesser tuberosity in place since this is somewhat displaced from the lateral rib, which itself tends to be embedded in the region where the greater tuberosity is or should be positioned.

Examples of successful shoulder prostheses include prostheses available under the trade designation "Neer II system" and "3M Modular Shoulder" from 3M Health Care Ltd., a subsidiary of Minnesota Mining and Manufacturing Company, St. Paul, Minn. Competing shoulder prostheses are also available. In addition, shoulder prostheses are disclosed, for example, in U.S. Pat. Nos. 3,916,451; 3,978,528; 4,179,758; 4,919,670; 4,919,669 and 5,462,563; PCT Patent Publication No. WO 96/17553; European Patent Publication Nos. EP 0 041 591; EP 0 127 503; EP 0 216 489; EP 0 299 889 and EP 0 639 359; British Patent Nos. GB 1,438,950 and GB 2,223,172; and German Patentschrift No. DE 195 09 037.

SUMMARY OF THE INVENTION

The present invention provides a proximal humeral prosthesis in which these problems are at least mitigated.

Generally, a proximal humeral prosthesis according to the invention comprises a head corresponding to the humeral head of a patient, and a stem having a proximal end to which the head is mounted. The stem extends at an oblique angle away from the head, and is adapted to be received in the proximal end of the humerus and to be fixed therein to hold the prosthesis in place so that the head then corresponds in position to that of the humeral head. The prosthesis has a central plane coincident with the longitudinal axis of the stem about which it has a mirror axis of symmetry. At least one, and preferably two, projecting ribs are positioned at or near the proximal end of the stem adjacent the head, with the projecting rib being offset relative to the center plane at an offset angle of from about 20° to about 40°.

When the stem is implanted in the medullary canal of the humerus, the radial direction of one of the ribs will be substantially aligned with the bicipital groove. Preferably each projecting rib is provided with means, such as holes, to suture one or both of a separated lesser or greater tuberosity in place. There may be, for example, three or four such holes.

With such an arrangement the opposed pair of ribs have a number of advantages. They will prevent rotation of the stem within the humerus and so no additional ribs are required just for this purpose, although other ribs may be desirable for mechanical reinforcement between the head and the stem and will then also help to prevent rotation. In addition, because the outer edge of one of the two ribs is going to be positioned near to the base of the bicipital groove, ready access to that rib can be obtained to suture a lesser tuberosity if that is broken and separated. That rib, or alternatively or additionally, the other ribs can be used to assist the suture of the greater tuberosity if that is separated or detached.

By having two ribs which are equally spaced from the central plane as defined above, then only a single prosthesis is required for a left shoulder or for a right shoulder. The invention however embraces the concept of providing a single rib, since only one such rib is required if one provides two different forms of prosthesis, i.e. one for a left shoulder and one for a right shoulder. Hospitals would, however, need to have both of these available for operations dependent upon whether the surgeon was operating on a left or right shoulder and this doubles the already quite large inventory required to meet the differing sizes required for differing patients. Therefore, where reference is made hereinafter to a pair of ribs or two ribs that reference, unless the context specifically requires otherwise, includes the possibility of a single rib.

These two ribs will generally have a thickness of the order of 1 to 3 mm. Preferably they are about 2 mm thick.

They preferably extend radially out from the stem by a distance of from 2 to 5 mm, and most preferably about 3 mm. Preferably they have a length measured parallel to the axis of the stem of from 20 to 35 mm, and most preferably about 32 mm.

These two projecting ribs are each desirably angled to the central plane at an angle of from 25 to 35°, more desirably 29 to 31°, and most preferably at an angle of about 30° so that there is an included angle between them of about 60°. These projecting ribs are preferably provided at substantially equal but opposite offset angles relative to the central plane (i.e., the plane of symmetry), although it will be understood that unequal offset angles could be provided, for example, on unique right and left shoulder prostheses rather than the preferred prosthesis, which can be used on either the right or left side.

In the included angle between the two ribs, it is desirable that the stem be hollowed out into a smooth scallop between the two ribs. This has the advantage that one can fill this region with bone chips and pull the tuberosities tightly against these, so that with the good blood supply to the tuberosities, this region should regenerate fresh bone which then assists in holding the prosthesis in place.

In other respects the prosthesis need not be any different from a conventional prosthesis, for example, the prostheses available under the trade names "Neer II" and "3M Modular Shoulder."

The stem may be arranged to be a cement-less fit within the medullary canal of the humerus or to be fixed in place by cement. The stem may be provided with one or more, preferably two, longitudinal grooves which may be slightly tapered to aid in pressurizing and extruding excess cement if cement is used.

Also, the stem itself is preferably slightly tapered, e.g. an included angle of about 1° and the hole made in the medullary canal to receive the stem will be very slightly undersize so that the stem is a tight fit. In the case of cement-less fixation, it is preferred that the proximal end of the stem be given an increased taper, e.g. an included angle of about 5°.

In practice a range of prostheses will be required with stems of differing diameter and length to suit patients of differing sizes and conditions.

The head will be formed as part of a sphere to engage with the patient's glenoid or if that is damaged with a glenoid replacement. The axis of the head medially relative to the axis of the stem to simulate the similar angling of the humeral head relative the humerus. The radial height of the head also needs to be chosen to suit a particular patient and so a range of prostheses with differing head heights will normally need to be available to the surgeon. As the radial head height increases, so will the overall size of the head increase. It is desirable, however, that the head should not extend significantly beyond the stem in the axial direction of the stem since otherwise the head can inflame the tendons of the rotator cuff. Therefore, with increasing head height, the head needs to be displaced, whilst keeping the angle of the head to the axis of the stem constant. Further, to ensure that the tendons of the rotator cuff and other tissue is not inflamed by joint movements, it is desirable that the lower portion of the head depart from a spherical shape and adopt a shape which smoothly joins the spherical shape of the head to the stem.

As explained above, a rib will normally be provided between the head and the stem to provide mechanical support for the part of the head which is displaced from alignment with the stem. This rib can conveniently be of a thickness of the order of from 1 to 3 mm and preferably be about 2 mm thick.

The prosthesis may be a so-called "monoblock" system where the head and stem are formed integrally. The Neer II system noted above is a monoblock system. Alternatively the prosthesis may be a modular system where the stem and head are separate and the head is fitted in place once the stem has be secured, the joint between the head and a projection from the stem being of the Morse taper type. The 3M Modular Shoulder noted above is of the latter type.

The prosthesis is preferably made from cobalt chrome steel, although other materials are also acceptable, such as titanium.

According to another aspect of the invention, there is provided a method of treating a fractured humerus where the lesser or greater tuberosity or both have become fractured in an accident or separated as a result of other trauma. This method generally comprises the following steps:

(a) resecting the end of the humerus to remove the humeral head;

(b) providing a proximal humeral prosthesis comprising:
a head corresponding to the humeral head of a patient; and
a stem having a proximal end to which the head is mounted, the stem extending at an oblique angle away from the head, the stem being adapted to be received in the proximal end of the humerus and to be fixed therein to hold the prosthesis in place so that the head then corresponds in position to that of the humeral head, the prosthesis having a central plane coincident with the longitudinal axis of the stem about which it has a mirror axis of symmetry; and
a projecting rib positioned at or near the proximal end of the stem adjacent the head, the projecting rib being offset relative to the center plane at an offset angle approximating the position of the greater or lesser tuberosity of the humerus (c) inserting the stem into the proximal end of the humerus and aligning the projecting rib with the bicipital groove;

(d) after the step (c), suturing one of the lesser and greater tuberosity to the projecting rib.

Preferably, a plurality of holes are provided in the projecting rib; and the suturing step includes passing a suture through one of the holes in the projecting rib. Also, preferably, a scallop is formed in the stem adjacent the projecting rib and generally in alignment with the central plane. The scallop is filled with bone chips and the tuberosities are pulled tightly against the bone chips with the suture.

Most preferably, the projecting rib constitutes a first projecting rib, and the prosthesis further includes a second projecting rib a positioned at or near the proximal end of the stem adjacent the head. The second projecting rib is offset relative to the center plane in the direction opposite the first projecting rib at an angle substantially equal to the offset angle. The first and second projecting ribs each having a plurality of holes formed therethrough. The suturing step preferably then includes passing a suture through one of the holes in each of the projecting ribs. Also, preferably, the scallop is formed in the stem between the projecting ribs.

Other features will be pointed out hereinafter.

BRIEF DESCRIPTION OF THE DRAWING

The invention will now be described, by way of example, with reference to the accompanying drawings, in which.

DESCRIPTION OF PREFERRED EMBODIMENTS

Figure 1:
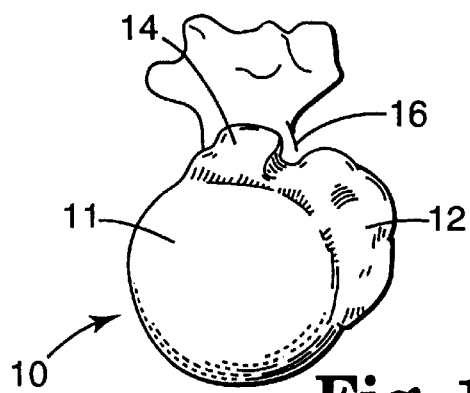
FIG. 1 is diagram of the end of a humerus showing the various component parts.

FIG. 1 shows a typical proximal end to a humerus 10. There is a rounded humeral head 11 which forms the actual joint with the scapula. Positioned around that humeral head 11 is the greater tuberosity 12 and the lesser tuberosity 14 and between these two is a groove 16 known as the bicipital groove.

Figure 4:
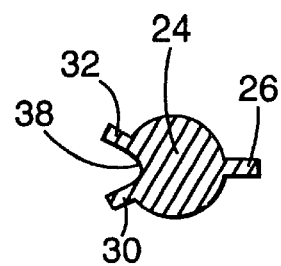
FIG. 4 is a section on the line 4—4 of FIG. 2.
Figure 3:
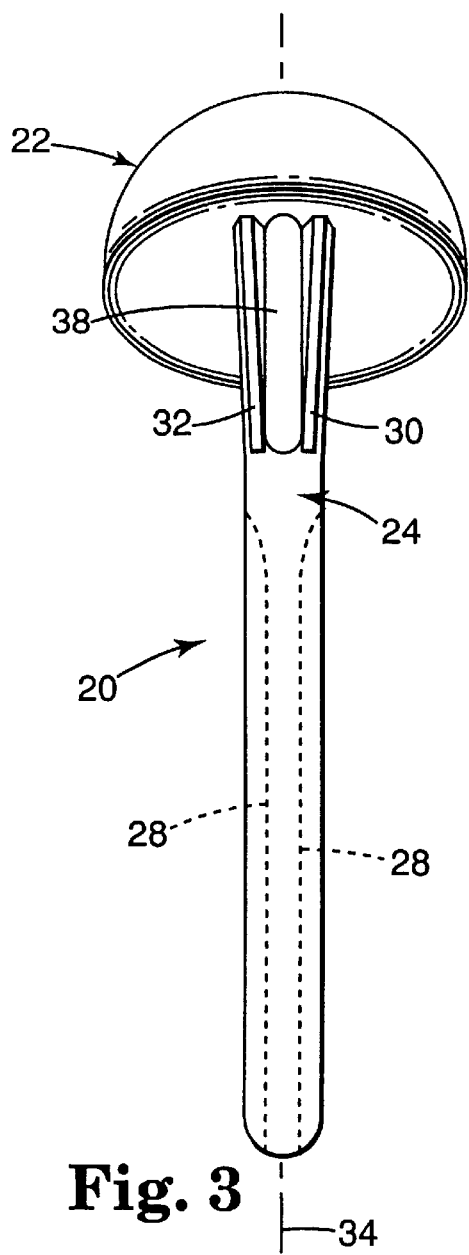
FIG. 3 is an elevation taken at right angles to the view of FIG. 2.
Figure 2:
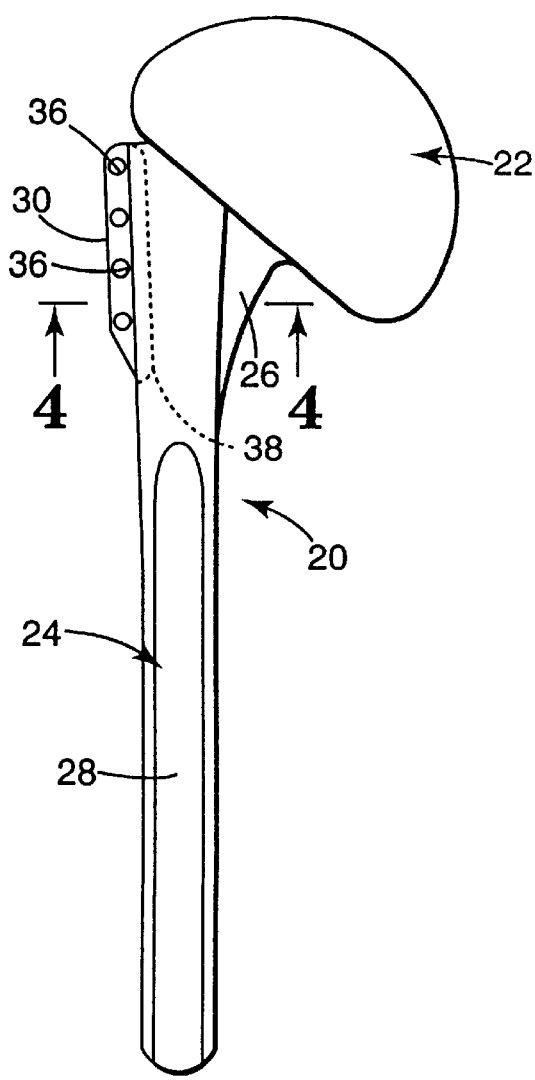
FIG. 2 is a side view of one embodiment of a humeral prosthesis according to the invention.

FIGS. 2 to 4 show a humeral prosthesis 20 according to the invention. It comprises a head 22 and a stem 24, which are preferably integrally formed from cobalt chrome steel with a supporting rib 26 extending between them. The stem 24 also has longitudinal grooves 28. The stem 24 is arranged to fit into the medullary canal with the head 22 positioned to replace the humeral head 11.

Figure 5:
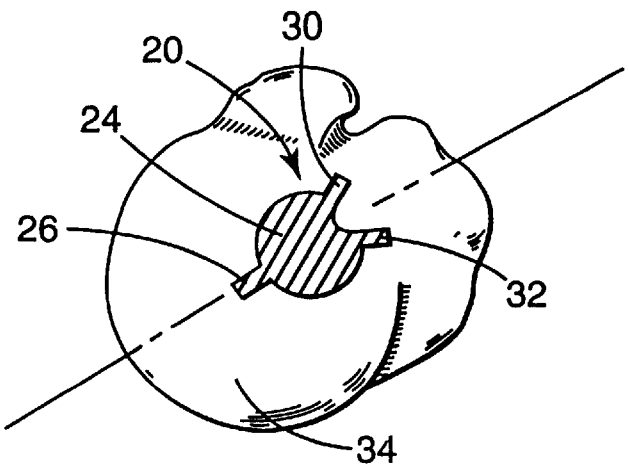
FIG. 5 is a diagram similar to FIG. 1 showing superimposed the section of a humeral prosthesis according to the invention.

The prosthesis 20 according to the invention also has a pair of projecting ribs 30 and 32. These projecting ribs 30 and 32 are spaced equally by an offset angle which is approximately 30° from the central axis of the stem 24 and about which the prosthesis 20 is a mirror image. It can be seen from FIG. 5 that one is approximately aligned in a direction leading directly towards the bicipital groove. The other would be so aligned in the case of the other shoulder of a patient.

The projecting ribs 30 and 32 have holes 36. These holes constitute one example of a means in the projecting ribs 30, 32 for securing bone tissue to the prosthesis 20. As shown the ribs 30 and 32 can be used to suture a lesser tuberosity that has become misplaced. In addition that projecting rib 30 can also be used to suture on a greater tuberosity and if necessary the other projecting rib 32 can additionally be used for suturing the greater tuberosity.

An additional advantage in having the two projecting ribs 30 and 32 which are equally spaced from the central axis 34 is that a single prosthesis will now act both for the left shoulder and the right shoulder joint, and these two ribs provide security against rotation of the stem 24 in the humerus.

Between the two ribs 30 and 32 the stem has a hollowing or scallop 38. As explained above, this provides a region in which fresh bone growth can be stimulated to assist in fixing the prosthesis 20 in place.

Figure 6:
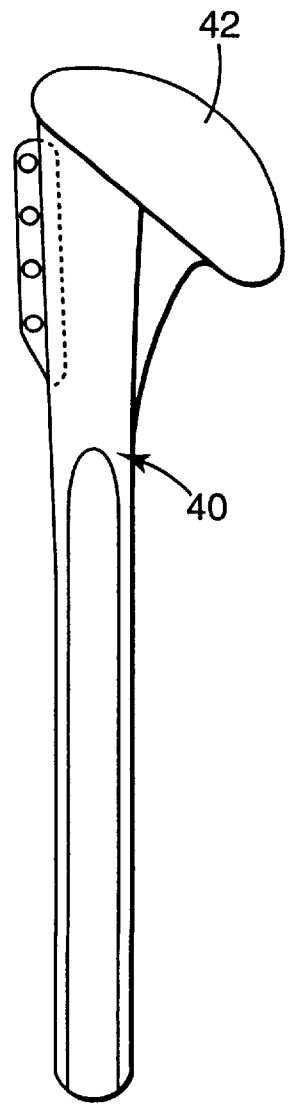
FIG. 6 is a view similar to FIG. 2 of another prosthesis according to the invention.

Normally a range of sizes of prosthesis are provided to suit individual patients. The prosthesis 40 shown in FIG. 6 has a smaller head 42. It will be noted however that, whilst it is still angled at the same angle to the axis 34 of the stem, the head 42 is not displaced in the lateral direction as far as the head 22 of the prosthesis 20 so that the edge of neither head projects significantly beyond the respective stem.

As various changes could be made in the above constructions and methods without departing from the scope of the invention as defined in the claims, it is intended that all matter contained in the above description or shown in the accompanying drawings be interpreted as illustrative and not in a limiting sense.

We claim:

1. A proximal humeral prosthesis comprising:
   a head corresponding to the humeral head of a patient; and
   a stem having a proximal end to which the head is mounted, the stem extending at an oblique angle away from the head, the stem being adapted to be received in the proximal end of the humerus and to be fixed therein to hold the prosthesis in place so that the head then corresponds in position to that of the humeral head, the head and stem having a central plane coincident with the longitudinal axis of the stem about which it has a mirror axis of symmetry; and
   no more than three ribs each extending only along a portion of the length of the stem including at least:
      a projecting rib positioned at or near the proximal end of the stem adjacent the head, the projecting rib being offset relative to the center plane at an offset angle of from about 20° to about 40°, a smooth scallop being hollowed out of the stem in a region of the stem defined between the rib and the center plane and a corresponding mirror portion on the other side of the center plane; and
      a supporting rib projecting from the stem adjacent the proximal end of the stem, the supporting rib being disposed along the center plane in the direction generally opposite the projecting rib.

2. The proximal humeral prosthesis according to claim 1 in which the projecting rib constitutes a first rib, the prosthesis further comprising a second projecting rib positioned at or near the proximal end of the stem adjacent the head, the second projecting rib being offset relative to the center plane in the direction opposite the first projecting rib.

3. The proximal humeral prosthesis according to claim 1 in which the stem has a pair of elongate grooves extending longitudinally along the stem adjacent the distal end of the stem.

4. The proximal humeral prosthesis according to claim 1 in which the projecting rib has a thickness of the order of 1 to 3 mm.

5. The proximal humeral prosthesis according to claim 4 in which the projecting rib extends radially out from the stem by a distance of from 2 to 5 mm.

6. The proximal humeral prosthesis according to claim 5 in which the projecting rib has a length measured parallel to the axis of the stem of from 20 to 35 mm.

7. The proximal humeral prosthesis according to claim 6 in which the offset angle is from about 25° to about 35°.

8. The proximal humeral prosthesis according to claim 1 further comprising means in the projecting rib for securing bone tissue to the prosthesis.

9. The proximal humeral prosthesis according to claim 8 wherein the means in the projecting rib for securing bone tissue to the prosthesis comprises a plurality of holes formed in the projecting rib.

10. A proximal humeral prosthesis comprising:
    a head corresponding to the humeral head of a patient; and
    a stem having a proximal end to which the head is mounted, the stem extending at an oblique angle away from the head, the stem being adapted to be received in the proximal end of the humerus and to be fixed therein to hold the prosthesis in place so that the head then corresponds in position to that of the humeral head, the head and stem having a central plane coincident with the longitudinal axis of the stem about which it has a mirror axis of symmetry; and
    a plurality of ribs consisting essentially of:
       a pair of projecting ribs positioned at or near the proximal end of the stem adjacent the head and extending along only a portion of the length of the stem, the protecting ribs being offset in opposite directions relative to the center plane at substantially identical offset angles of from about 20° to about 40°; and
       a supporting rib projecting from the stem adjacent the proximal end of the stem, the supporting rib being disposed along the center plane in the direction generally opposite the projecting ribs.

11. The proximal humeral prosthesis according to claim 10 in which the stem has a pair of elongate grooves extending longitudinally along opposite sides of the stem adjacent the distal end of the stem, the grooves extending along a plane generally perpendicular to the center plane.

12. The proximal humeral prosthesis according to claim 10 further comprising means in the projecting ribs for securing bone tissue to the prosthesis.

13. The proximal humeral prosthesis according to claim 12 wherein the means in the projecting ribs for securing bone tissue to the prosthesis comprises a plurality of holes formed in the projecting ribs.

14. The proximal humeral prosthesis according to claim 13 in which the projecting ribs have a thickness of the order of 1 to 3 mm.

15. The proximal humeral prosthesis according to 14 in which the projecting ribs have a thickness of about 2 mm.

16. The proximal humeral prosthesis according to claim 14 in which the projecting ribs extend radially out from the stem by a distance of from 2 to 5 mm.

17. The proximal humeral prosthesis according to claim 16 in which the projecting ribs extend radially out from the stem by a distance of about 3 mm.

18. The proximal humeral prosthesis according to claim 16 in which the projecting ribs have a length measured parallel to the axis of the stem of from 20 to 35 mm.

19. The proximal humeral prosthesis according to claim 18 in which the projecting ribs have a length measured parallel to the axis of the stem of about 32 mm.

20. The proximal humeral prosthesis according to claim 18 in which the offset angles are from about 25° to about 35°.

21. The proximal humeral prosthesis according to claim 20 in which the offset angles are from about 29° to about 31°.

22. A method of treating a fractured humerus where the lesser or greater tuberosity or both have become fractured in an accident or separated as a result of other trauma, the humerus including a bicipital groove between the lesser and greater tuberosity, the method comprising the following steps:
(a) resecting the end of the humerus to remove the humeral head;
(b) providing a proximal humeral prosthesis comprising:
a head corresponding to the humeral head of a patient; and
a stem having a proximal end to which the head is mounted, the stem extending at an oblique angle away from the head, the stem being adapted to be received in the proximal end of the humerus and to be fixed therein to hold the prosthesis in place so that the head then corresponds in position to that of the humeral head, the prosthesis having a central plane coincident with the longitudinal axis of the stem about which it has a mirror axis of symmetry; and
a projecting rib positioned at or near the proximal end of the stem adjacent the head, the projecting rib being offset relative to the center plane at an offset angle approximating the position of the greater or lesser tuberosity of the humerus
(c) inserting the stem into the proximal end of the humerus and aligning the projecting rib with the bicipital groove;
(d) after the step (c), suturing one of the lesser and greater tuberosity to the projecting rib.

23. The method according to claim 22 wherein a plurality of holes are provided in the projecting rib; the step (d) including passing a suture through one of the holes in the projecting rib.

24. The method according to claim 22 wherein the projecting rib constitutes a first projecting rib, and the prosthesis further includes a second projecting rib a positioned at or near the proximal end of the stem adjacent the head, the second projecting rib being offset relative to the center plane in the direction opposite the first projecting rib at an angle substantially equal to the offset angle; the first and second projecting ribs each having a plurality of holes formed therethrough; the step (d) including passing a suture through one of the holes in each of the projecting ribs.

25. A method of treating a fractured humerus where the lesser or greater tuberosity or both have become fractured in an accident or separated as a result of other trauma, the humerus including a bicipital groove between the lesser and greater tuberosity, the method comprising the following steps:
(a) resecting the end of the humerus to remove the humeral head;
(b) providing a proximal humeral prosthesis comprising;
a head corresponding to the humeral head of the patient; and
a stem having a proximal end to which the head is mounted, the stem extending at an oblique angle away from the head the stem being adapted to be received in the proximal end of the humerus and to be fixed therein to hold the prosthesis in place so that the head then corresponds in position to that of the humeral head, the prosthesis having a central plan coincident with the longitudinal axis of the stem about which it has a mirror axis of symmetry; and
a protecting rib positioned at or near the proximal end of the stem adjacent the head, the projecting rib being offset relative to the center plane at an offset angle approximating the position of the greater or lesser tuberosity of the humerus, and the projecting rib having a plurality of holes formed therethrough, wherein a scallop is formed in the stem adjacent the projecting rib and generally in alignment with the central plane;
(c) inserting the stem into the proximal end of the humerus and aligning the projecting rib with the bicipital groove;
(d) filling the scallop with bone chips and pulling the tuberosities tightly against the bone chips; and
(e) after the step (d), suturing one of the lesser and greater tuberosity to the projecting rib by passing a suture through one of the holes in the projecting rib.

26. A method of treating a fractured humerus where the lesser or greater tuberosity or both have become fractured in an accident or separated as a result of other trauma, the humerus including a bicipital groove between the lesser and greater tuberosity, the method comprising the following steps:
(a) resecting the end of the humerus to remove the humeral head;
(b) providing a proximal humeral prosthesis comprising:
a head corresponding to the humeral head of the patient; and
a stem having a proximal end to which the head is mounted, the stem extending at an oblique angle away from the head, the stem being adapted to be received in the proximal end of the humerus and to be fixed therein to hold the prosthesis in place so that the head then corresponds in position to that of the humeral head, the prosthesis having a central plan coincident with the longitudinal axis of the stem about which it has a mirror axis of symmetry; and
a projecting rib comprising a first projecting rib and a second projecting rib, the first and second projecting ribs positioned at or near the proximal end of the stem adjacent the head, the first projecting rib being offset relative to the center plane at an offset angle approximating the position of the greater or lesser tuberosity of the humerus, the second protecting rib being offset relative to the center plain in the direction opposite the first projecting rib at an angle substantially equal to the offset angle, and the projecting ribs each having a plurality of holes formed therethrough, wherein a scallop is formed in the stem adjacent the projecting rib and generally in alignment with the central plane;

(c) inserting the stem into the proximal end of the humerus and aligning the projecting rib with the bicipital groove;

(d) filling the scallop with bone chips and pulling the tuberosities tightly against the bone chips; and (e) after the step (d), suturing one of the lesser and greater tuberosity to the projecting rib by passing a suture through one of the holes in the projecting rib.

* * * * *